United States Patent [19]

Werbel et al.

[11] Patent Number: 4,515,793

[45] Date of Patent: May 7, 1985

[54] PHENYLPIPERAZINES WHICH ARE USEFUL IN THE TREATMENT OF SCHISTOSOMIASIS

[75] Inventors: Leslie M. Werbel, Ann Arbor; Norman Colbry, Gregory; William Turner, Ypsilanti; Donald F. Worth, Ann Arbor, all of Mich.

[73] Assignee: Edna McConnell Clark Foundation, New York, N.Y.

[21] Appl. No.: 517,883

[22] Filed: Jul. 27, 1983

[51] Int. Cl.³ ............... A61K 31/495; C07D 241/04; C07D 405/06

[52] U.S. Cl. .................................. 514/252; 544/121; 544/364; 544/375; 544/376; 544/379; 544/392; 544/394; 544/395; 260/239 A; 514/255

[58] Field of Search ............ 544/392, 394, 364, 375, 544/379; 424/250

[56] References Cited

PUBLICATIONS

Geiszler, "Chemical Abstracts", vol. 80, 1974, Col. 83055x.

Primary Examiner—Glennon H. Hollrah
Assistant Examiner—James H. Turnipseed
Attorney, Agent, or Firm—Sprung, Horn, Kramer & Woods

[57] ABSTRACT

A compound of the formula

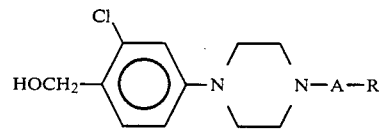

in which
A is

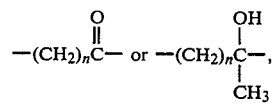

n is 1, 2 or 3, and

R is phenyl optionally substituted with halogen, alkyl, phenyl, cyano, hydroxy, alkoxy, mercapto, sulfinyl, sulfonyl, amino, nitro, trifluoromethyl and/or naphthyl radicals; or a furan, thiophene, pyridine, benzofuran, dibenzothiophene or thianthrene radical, or a pharmacologically acceptable salt thereof, for treating schistosomiasis.

4 Claims, No Drawings

PHENYLPIPERAZINES WHICH ARE USEFUL IN THE TREATMENT OF SCHISTOSOMIASIS

The present invention relates to novel phenylpiperazines which are useful in the treatment of schistosomiasis.

U.S. Pat. No. 3,558,629 and its continuation-in-part U.S. Pat. No. 3,714,167 disclose as active against schistosomiasis compounds of the formula

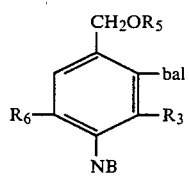

where hal is halo, i.e. chloro, bromo, iodo or fluoro: $R_3$, $R_5$ and $R_6$ are each hydrogen or lower-alkyl; NB is $N(R)-Y-NR_1R_2$ or

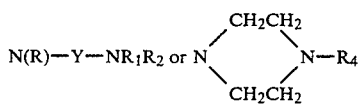

R is hydrogen or lower-alkyl; Y is polycarbon-lower-alkylene; $R_1$ and $R_2$ are each hydrogen or lower-alkyl, lower-alkenyl or lower-hydroxyalkyl and can be the same or different; $R_1$ and $R_2$ taken with N also comprehend saturated N-heteromonocyclic radicals having from five to six ring atoms, illustrated by piperidino, pyrrolidino, morpholino, piperazino, hexamethyleneimino and lower-alkylated derivatives thereof; and, $R_4$ is hydrogen, lower-alkyl, lower-alkenyl, lower-hydroxyalkyl, carbamyl, thiocarbamyl, lower-alkanoyl, lower-carbalkoxy, carboxy-(lower-alkanoyl) or phenyl-X-(lower-alkyl), where X is oxygen or a direct linkage.

U.S. Pat. No. 4,234,583 discloses as active against schistosomiasis compounds of the formula

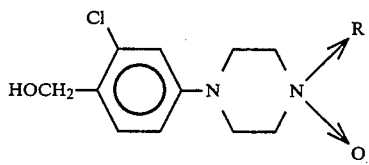

and acid addition salts thereof wherein R is methyl, ethyl, propyl or isopropyl preferably wherein R is methyl.

While such compounds are effective it is desirable to provide a different class of compounds also characterized by high activity and low mutagenicity.

Accordingly, in accordance with the present invention there are provided compounds of the formula

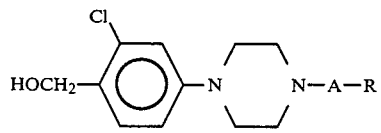

in which
A is

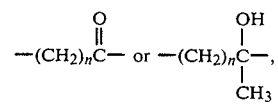

n is 1, 2 or 3, and

R is phenyl optionally substituted with halogen, alkyl, phenyl, cyano, hydroxy, alkoxy, mercapto, sulfinyl, sulfonyl, amino, nitro, trifluoromethyl and/or naphthyl radicals; or a furan, thiophene, pyridine, benzofuran, dibenzothiophene or thianthrene radical, or pharmacologically acceptable salts thereof.

Preferred sub-groups are those compounds in which

R is phenyl optionally substituted with up to 3 radicals independently selected from halogen, alkyl of up to 4 carbon atoms, phenyl, cyano, hydroxy, alkoxy of up to 4 carbon atoms, mercapto, phenylmercapto, phenylsulfinyl, phenylsulfonyl, amino, nitro, trifluoromethyl, naphthyl, and alkylmercapto, alkylsulfinyl and alkylsulfonyl of up to 4 carbon atoms, or R is a furan, thiophene, pyridine, benzofuran, dibenzothiophene or thianthrene radical optionally substituted by halogen and/or alkyl of up to 4 carbon atoms.

The novel compounds can be prepared by several different routes. Reaction variant (a) generally follows U.S. Pat. No. 3,714,167 and is outlined as follows:

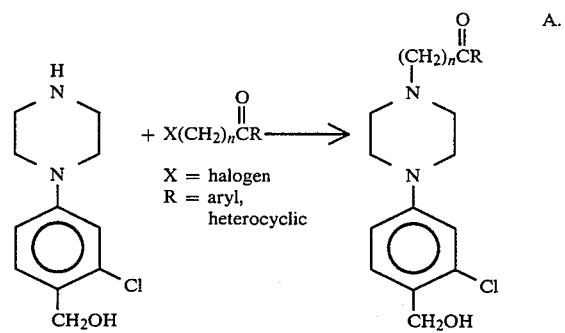

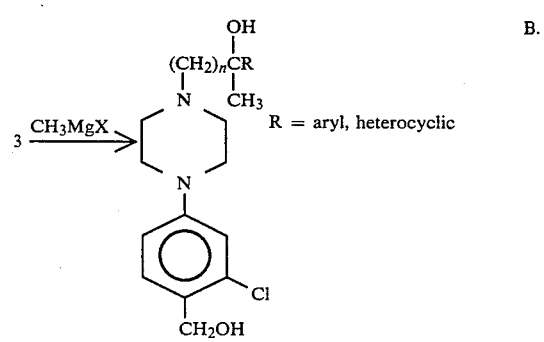

-continued

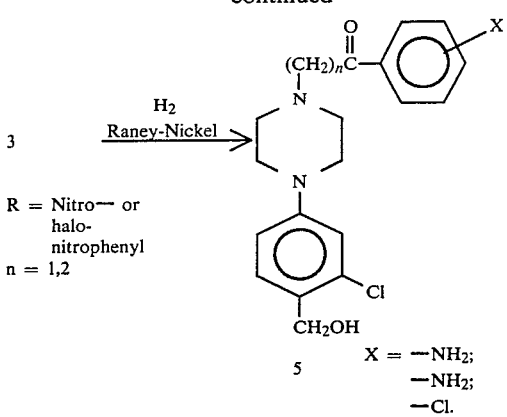

3

R = Nitro— or halo-nitrophenyl
n = 1,2

X = —NH$_2$;
—NH$_2$;
—Cl.

Starting material I is known from U.S. Pat. No. 3,714,167. Some of the side chain intermediates 2 are available commercially as chloro or bromo derivatives (X=Cl, Br). Others can be synthesized by known procedures, outlined in reaction variant (b) hereinbelow. The coupling reaction, Reaction A, is preferably carried out at room temperature or below.

Amino analogs 5 of step C can be prepared by catalytic reduction of the corresponding nitro compounds under neutral conditions at approximately three atmospheres of hydrogen. These conditions avoid possible reduction of the benzyl alcohol moiety or dehalogenation. Tetrahydrofuran is the preferred solvent.

Reaction variant (b) involves the following steps:

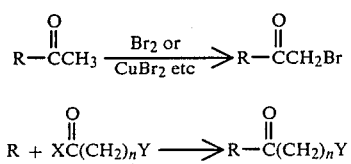

R=aryl, heterocyclic
X=halogen
Y=halogen when n=2; halogen or H when n=1.

Higher temperatures generally give poor yields, but are nonetheless desirable in some examples, especially when n=3. At least one equivalent of triethylamine or potassium carbonate can be added to neutralize the acid generated, but a moderate excess of base is not detrimental to the reactions. Triethylamine is the preferred base. A wide variety of solvents may be used but acetone, tetrahydrofuran, and methanol are preferred. Purification of products can be carried out by crystallization (lower alcohols, ethyl acetate, and acetonitrile are preferred) and column chromatography. Some analogs decompose slowly if kept in solution. This is especially true of polyhalogenated compounds. Thus, extended times of reaction, except at lower temperatures, is generally to be avoided.

As noted, some products can be used as reactants i.e. 3 in step B of reaction variant (a).

The novel compounds for the most part are white or light beige to yellow. They are solids which are stable under normal atmospheric conditions and have moderate melting points.

They are generally soluble in common organic solvents (DMSO, DMF, chloroform) but are not soluble in water.

They are weak bases and readily form acid addition salts some of which have greater water solubility than the free bases. Representative acids include any of those which are pharmacologically acceptable, e.g. hydrochloric acid, sulfuric acid, benzoic acid, acetic acid, citric acid, etc.

In accordance with the invention, oral pharmaceutical compositions are produced by formulating a compound of the invention, optionally with other active ingredients, in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into a teaspoon or other standard container. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg., preferably 5 to 100 mg., of the active ingredient per dosage unit so that the entire amount to be administered during a day can be made up from a reasonable number of dosage units.

The compounds of the invention may be administered parenterally, especially intramuscularly, in a suitable vehicle, such as isotonic saline solutions, which may contain other active ingredients, buffering agents, preservatives, etc.

The aforementioned compounds are administered in dosage unit form, with the dose adjusted to the needs and tolerances of the individual patient. The usual mammalian dosage range for a 70 kg. subject is from 10 to 1000 mg. per day (0.1 mg. to 14 mg. per kg. of weight per day), preferably 50 to 250 mg. per day (0.7 mg. to 3.6 mg. per kg. of weight per day), optionally in divided portions.

Preparation of the novel compounds is shown in the following illustrative examples wherein temperatures are in °C. unless otherwise stated.

EXAMPLE 1

2-Bromo-2',3',4'-trichloroacetophenone

A mixture of 2',3',4'-trichloroacetophenone (21.4 g, 0.0958 mole), anhydrous sodium acetate (8.0 g), and n-hexane (50 ml) was heated under reflux while treated with a solution of bromine (15.3 g, 0.096 mole) in 25 ml of n-hexane in five portions, decolorizing before each new addition. The mixture was then filtered while hot and the insoluble residue was triturated twice with 50 ml of boiling n-hexane. Enough additional n-hexane was added to the combined filtrates to avoid oiling out of product at 40°. The solution was then seeded and cooled at −10° for 18 hours. Product was collected and air dried to give 17.9 g (62%), mp 44°–46°.

2-[4-[3-Chloro-4-(hydroxymethyl)phenyl]-1-piperazinyl]-1-(2,3,4-trichlorophenyl)ethanone A solution of 2-chloro-4-(1-piperazinyl)-benzenemethanol (8.0 g, 35 m mole) in 75 ml of tetrahydrofuran (THF) and 5 ml of triethylamine was added during ten minutes to a cold (0°–5°) solution of 2-bromo-2',3',4'-trichloroacetophenone in 25 ml of THF. After the addition, the mixture was stirred at 0° for 0.5 hours and at 25° for three hours. The mixture was then stored at −10° for 18 hours and filtered. The filtrate was evaporated at reduced pressure (35°) to give a light yellow solid which was recrystallized twice from ethanol (250 ml) to afford 8.3 g (63%), mp 133°–135° (Compound 8, Table 1).

Prepared in like manner were compounds 1 to 7, 9 to 21, 23, 24 and 27.

The appropriate 2-halo-acetophenone intermediates for preparation of compounds 1, 2, 3, 7 and 19 were commercially available.

The 2-bromoacetophenone intermediates for preparation of compounds 9 to 11 were prepared from the corresponding commercially available acetophenones and cupric bromide.

The 2-bromoacetophenone intermediates for the following compounds were prepared from appropriate commercially available acetophenones and bromine in the indicated solvent: 4, 5, 12 and 14 in acetic acid; 6 and 23 in dichloromethane; and 15, 16, 17, 20, 21, 24 and 27 in chloroform.

The 2-bromoacetophenone intermediate for compound 13 was prepared from commercially available 1,2,4-trichlorobenzene by Friedel-Crafts acetylation followed by bromination as in Example 1.

The 2-bromoacetophenone intermediate for compound 18 was prepared from commercially available 3-chlorophenol by acetylation [F. Cramer and O. H. Elschnig, Chem Ber., 89 1 (1956)] followed by a Fries rearrangement and bromination with cupric bromide.

EXAMPLE 2

2-[4-[3-Chloro-4-(hydroxymethyl)phenyl]-1-piperazinyl]-1-(3-aminophenyl)-ethanone (Cpd. 25)

A solution of 2-[4-[3-chloro-4-(hydroxymethyl)-phenyl]-1-piperazinyl]-1(3-nitrophenyl)ethanone (1.5 g, 3.8 m mole) in 100 ml of tetrahydrofuran was catalytically reduced at 25° over 0.5 g of Raney-Nickel with an average of three atmospheres of hydrogen. When the theoretical amount of hydrogen had been absorbed, the mixture was filtered and the filtrate was evaporated at reduced pressure to give a yellow solid which was recrystallized from acetonitrile to afford 0.95 g (69%), mp 174.5°–180° (Table 1). Prepared in the like manner were Cpd. 37 (Table 2) and 26 (Table 1).

EXAMPLE 3

3-[4-[3-Chloro-4-(hydroxymethyl)phenyl]-1-piperazinyl]-1-(4-chlorophenyl)-1-propanone (Cpd. 28)

A mixture of 3.0 g (0.013 mole) of 2-chloro-4-(piperazinyl)benzenemethanol, 2.7 g (0.013 mole) of 3,4'-dichloropropiophenone, and 1.3 g (0.014 mole) of triethylamine in 80 ml of acetone was stirred at room temperature for 22 hours and filtered. The filtrate was concentrated to dryness in vacuo and the residue was triturated with cold methanol to obtain a solid. Recrystallization from acetonitrile gave 3.5 g (67%) of gold needles, mp 130°–134° (Table 2).

Prepared in like manner were compounds 29–36 and 38–44 (Table 2). Compound 37 was prepared by reduction of compound 35.

The intermediate 3-chloropropiophenones for preparation of compounds 29 to 44 were synthesized from appropriate commercially available substituted benzenes and 3-chloropropionyl chloride by the Friedel-Crafts condensation.

The intermediate 3-chloropropiophenone for preparation of compound 38 by oxidation with acetyl nitrate of 3-chloro-4'-thiomethylpropiophenone (which was used to synthesize Cpd. 31). Oxidation of the latter compound with hydrogen peroxide gave 3-chloro-4'-methylsulfonylpropiophenone which was used to prepare Cpd. 32.

Nitration of 3,4'-dichloropropiophenone gave 3,4'-dichloro-3'-nitropropiophenone, the intermediate leading to compound 35.

EXAMPLE 4

2-[4-[3-Chloro-4-(hydroxymethyl)phenyl]-1-piperazinyl]-1-(2-benzofuranyl)-ethanone (Cpd. 49)

A solution of 2-acetylbenzofuran (3.2 g. 0.02) in ether (50 ml) was treated with bromine (3.2 g., 0.02 mole) portionwise at room temperature. The mixture rapidly decolorized to a light yellow solution that was poured into cold aqueous sodium bicarbonate. The layers were separated and the aqueous layer was extracted with ether. The combined ether extracts were dried ($K_2CO_3$) and the ether was removed in vacuo, keeping the mixture cold. The gummy, off-white solid was dissolved in acetone (50 ml) and quickly added to a solution of 2-chloro-4-(1-piperazinyl)benzenemethanol (4.0 g, 0.0176 mole) and triethylamine (2.0 g, 0.902 mole) in acetone (200 ml). The mixture was stirred at room temperature for one hour, then cooled in an ice bath. The solid was collected, washed with ether, and air dried. Recrystallization from acetone-ethanol gave 3.7 g (55%), mp 169°–172°.

Prepared in like manner were compounds 45 to 48 and 50 to 56 (Table 3).

The intermediate for preparation of compounds 55 and 56 were made by bromination of the products from the Friedel-Crafts acetylation of thianthrene dibenzothiophene, respectively.

EXAMPLE 5

3-Chloro-1-(2-furanyl)-1-propanone

At 25°, 3-chloropropionyl chloride (25.4 g, 0.20 mole) was added to a suspension of anhydrous aluminum chloride (27.1 g, 0.20 mole) in 1,2-dichloroethane (DCE). The mixture was stirred until the aluminum chloride had nearly dissolved. This solution was added at 0°–5° during 15 minutes to a solution of furan (13.6 g, 0.2 mole) in 100 ml of DCE. The reaction mixture became very dark and a tan precipitate was deposited. The reaction mixture was then immediately poured into 1 of ice-water. An emulsion of some brown precipitate formed. This mixture was extracted with diethyl ether (five times, 150 ml), and the combined ether extract was filtered through a column of 150 g of silica gel. The column was then washed with 200 ml of ether and the combined eluants were concentrated at reduced pressure (40°) to 100 ml. The solution was then washed with 100 ml of saturated sodium hydrogen carbonate, dried over anhydrous sodium sulfate, treated with activated carbon, and evaporated at reduced pressure to give a liquid (3.5 g) which rapidly darkened at room temperature. It was stored at −10°. PMR spectroscopy indicated the product was about 75% desired copound. The mixture was used without further purification.

2-[4-[3-Chloro-4-(hydroxymethyl)phenyl]-1-piperazinyl]-1-(2-furanyl)-1-propanone (Cpd. 57)

At ∼25°, a solution of 2-chloro-4-(1-piperaziny)-benzenemethanol 3.0 g, 13.2 mmole) in 30 ml of tetrahydrofuran and 4 ml of triethylamine was added during five minutes to a solution of 3-chloro-1-(2-furanyl)-1-propanone (2.8 g. 13.3 mmole based on 75% purity). The mixture was stirred at 25° for one hour (a white precipitate formed) and was then heated under reflux for one half hour. The mixture was then filtered and the filtrate was evaporated at reduced pressure (<40°) to give an orange, heavy oil. The oil was triturated at 25° first with petroleum ether (30°–60°; two times, 50 ml) and then with diethyl ether. The orange-brown solid was collected, washed with a little diethyl ether, recrystallized from 25 ml of toluene, and finally triturated with diethyl ether (two times, 20 ml) and dried to give 3.10 g (67%), mp 95°–98° (Table 3).

EXAMPLE 6

4-[4-[3-Chloro-4-(hydroxymethyl)phenyl]-1-piperazinyl]-1-(2-thienyl)-1-butanone (Cpd. 58)

A solution of 2-chloro-2-butyrothienone (5.0 g, 0.026 mole, Aldrich), 2-chloro-4-(1-piperazinyl)benzenemethanol (5.65 g, 01025 mole) and triethylamine (2.6 g, 0.025 mole) in acetone (250 ml) was treated with a solution of potassium iodide (4.2 g, 0.026 mole) in N,N-dimethylformamidde (75 ml). The resulting solution was heated under reflux for four days, cooled to room temperature and poured into water (600 ml). The solid that formed was collected, washed with water, and recrystallized from acetone (100 ml) to give 4.5 g (48%) of crude product, mp 131°–133°. This solid was combined with 2.0 g of similar material and recrystallized from acetone to obtain tan crystals, mp 132°–133° (Table 3).

EXAMPLE 7

1-(4-Chlorophenyl)-4-[4-[3-chloro-4-(hydroxymethyl)-phenyl]-1-piperazinyl]-1-butanone (Cpd. 59)

A solution of 4,4′-dichlorobutyrophenone (4.5 g, 20.7 mmole) in 25 ml of acetone was added to a warm suspension of 2-chloro-4-(1-piperazinyl)benzenemethanol (4.7 g, 20.7 mole) in 50 ml acetone and 2.5 ml of triethylamine. The reaction mixture was refluxed for four days, cooled at −10° for three hours, and then filtered. The product was washed with a little acetone, triturated on the filter with water (four times, 50 ml), and air dried. Recrystallization from acetonitrile (65 ml) gave 3.0 g (35%), mp 137°–139°.

Prepared in like manner was compound 60 (Table 4).

EXAMPLE 8

4-[3-Chloro-4-(hydroxymethyl)phenyl]β-(4-chlorophenyl)β-methyl-1-piperazineethanol (Cpd. 61)

A solution of 2-[4-[3-chloro-4-(hydroxymethyl]phenyl-1-piperazinyl]-1-(4-chlorophenyl)ethanone (1.50 g, 3.96 mmole) in 30 ml of tetrahydrofuran, maintained at 0°–5° under nitrogen was treated with 3.0 ml of a 3.2M solution (9.6 mmole) of methyl magnesium chloride in tetrahydrofuran. A thick precipitate formed. After heating under reflux for one half hour, an additional 50 ml of tetrahydrofuran and 15 ml of methyl Grignard solution (18 ml total) were added. All material then dissolved. The solution was heated under reflux for one hour and then cooled to 0°. Then 50 ml of saturated ammonium chloride was added. The mixture was filtered to remove insoluble inorganic salts and the filtrate was evaporated under vacuum. The residue was dissolved in a mixture of 75 ml of chloroform and 75 ml of water. The organic layer was separated, dried over magnesium sulfate, and evaporated under vacuum. The residue was dissolved in about 15 ml of methanol and the solution cooled at −10°. The solid product, 0.78 g, was collected. PMR spectroscopy showed the presence of 12% starting ketone. This product was combined with 1.20 g of similar material obtained by repeating the previous procedure. Chromatography over 30 g of silica gel using dichloromethane as eluant gave 1.2 g, which on recrystallization from 3 ml of ethanol gave 0.67 g (21%) mp 126°–130°.

Tests were conducted to determine the antischistosomal activity in mice and monkeys. The results of the mice tests are reported in Tables 1 to 4 along with the chemical identifications of the compounds synthesized and tested.

The mice tests were conducted as follows:

A. Preinfection Procedures: Purina Laboratory chow (Ralston-Purina) and water were given ad libitum. All mice were housed in hanging stainless steel cages, without bedding, five per cage. They were kept in a ward with an ambient temperature of 75° F. and a relative humidity of 50–55%. Therapeutic treatment was given on Day 40 post-infection.

B. Experimental Procedures: $CD_1$ white female mice were exposed by the tail immersion method for 30 minutes to 80 individually counted *S. mansoni* cercariae (WRAIR laboratory strain). The cercariae were obtained from pools of no less than 25 *Biophalaria glabrata* snails. Each experiment consisted of 118 mice divided into infected/water treated and infected/vehicle-treated controls, and infected/drug-treated groups (two dose levels) for six compounds. Groups of 12 mice each were treated with a compound synthesized and provided by the Warner-Lambert Company, Ann Arbor, Mich. at two dose levels. At the same time, five mice were sacrificed to establish worm burdens as infection controls. Three weeks after treatment, all remaining mice were sacrificed and perfused. Gross pathology (liver and intestines) was noted and graded (0 to +3). Worm burdens were determined and the sex of the worms recorded. Following perfusions the liver and intestines were removed and examined for the presence of liver or dead worms. Throughout the experiment, the mice were observed for overt signs of intoxication such as paralysis, anorexia, ataxia, and death. Drugs were administered orally in Emulphor EL.

In addition, toxicity testing for determination of lethality was done on each compound. This test was done in three mice.

C. Drug Treatment: Treatment consisted of a single oral dose. Each drug was give initially at two dose levels, 40 mg/kg and 125 mg/kg, SID×1. If an 80% or greater reduction in live worm burden was observed at the lower dose, the drug was retested at 40 and 20 mg/kg, SID×1.

D. Criteria Used to Evaluate Therapeutic Effectiveness:
Evaluation of activity was determined by examination of the animals at 23 to 28 days after treatment. The schistosomes remaining alive after treatment were counted in the perfusates of the hepatic portal system and in press preparation of the livers. In the same preparations, the relative numbers of dead and/or encapsulated (i.e., worms may or may not be dead) parasites and the relative degree of pathology were ascertained. The efficacy of each treatment was that percentage of the control infection represented by the difference between numbers of parasites recovered from control ($H_2O$+vehicle) and treated animals. Thus, % efficacy is:

$$\frac{\text{Average of No. of Worms From Experimentally Treated Mice}}{\text{Average of No. of Worms From } H_2O + \text{vehicle controls}}$$

The high activity of the novel compounds can be seen in Tables 1 to 4.

TABLE 1

Antischistosomal Activity Reported For 2-[4-[3-Chloro-4-(hydroxymethyl)-phenyl-1-piperazinyl]-1-phenylethanones Administered in Single Oral Doses to Mice

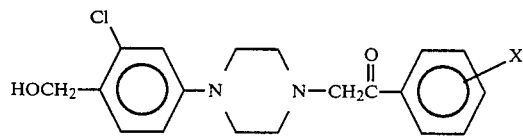

| | | | | % Reduction Live Worm Burden | | |
|---|---|---|---|---|---|---|
| Cpd. | X | mp (°C.) | Yield (%)[4] | 125 mg/kg | 40 mg/kg | 20 mg/kg |
| 1. | 4-Cl | 164–166 | 46 | 67 | 42 | |
| 2. | 4-F | 141–142 | 45 | 61 | 19 | |
| 3. | 2,4-$Cl_2$ | 132–134 | 21 | 94 | 81,86 | 62 |
| 4. | 4-$SO_2N(CH_2)_5$ | 178–181 | 67 | 66 | −10 | |
| 5. | 4-$NO_2$ | 143–146 | 67 | 98 | 74 | |
| 6. | 4-I | 159–163 | 60 | 83 | 62 | |
| 7. | 4-$CO_2C_6H_5$ | 189.5–192 | 75 | 0 | −20 | |
| 8. | 2,3,4-$Cl_3$ | 133–135 | 63 | 96[1] | 84 91[2] | |
| 9. | 2,3,4-$(OCH_3)_3$ | 136–139 | 47 | 30 | 13 | |
| 10. | 3,4,5-$(OCH_3)_3$ | 129–131 | 47 | 13[3] | −23 | |
| 11. | 4-$C(CH_3)_3$ | 127–132 | 64 | 59[3] | 16 | |
| 12. | 3-$NO_2$ | 148–150 | 78 | 73 | 31 | |
| 13. | 2,4,5-$Cl_3$ | 130–133 | 67 | 98 | 86,76 | 53 |
| 14. | 4-Cl,3-$NO_2$ | 142–143 | 59 | 99[3] | 56 | |
| 15. | 4-$CF_3$ | 142–144 | 82 | 79 | 43 | |
| 16. | 3,5-$Cl_2$ | 129–130.5 | 46 | 89 | 64 | |
| 17. | 2,4,5-$(CH_3)_3$ | 141–143 | 70 | 71[3] | 29 | |
| 18. | 4-Cl,2-OH | 174–176 | 26 | 26[3] | 5 | |
| 19. | 3,4-(CH=CH)$_2$ | 183.5–187 | 23 | 17 | −37 | |
| 20. | 2,5-$Cl_2$ | 124–126.5 | 34 | 99[3] | 65,80 | 72 |
| 21. | 2,4,6-$(CH_3)_3$ | 122–124 | 23 | 78 | 27 | |
| 22. | α,2-$(CH_2)_2$ | 130–132 | 24 | 87 | 73 | |
| 23. | 4-CN | 141.5–142.5 | 72 | 90 | 40 | |
| 24. | 2,3-(CH=CH)$_2$ | 154–159 | 70 | 64 | 3 | |
| 25. | 3-$NH_2$ | 174.5–180 | 69[5] | 46 | −11 | |
| 26. | 3-$NH_2$—4-Cl | 191–195 | 51[6] | 45 | −12 | |
| 27. | 3-Cl | 125–128 | 28 | 83 | 64 | |

[1]Dose, 156 mg/kg.
[2]Dose, 50 mg/kg.
[3]Dose, 160 mg/kg.
[4]Yield of reaction of the appropriate haloethyl phenyl ketone with 1-[3-chloro-4-(hydroxymethyl)-phenyl-]-piperazine, unless otherwise noted.
[5]Yield on reduction of Cpd. 12.
[6]Yield on reduction of Cpd. 14.

TABLE 2

Antischistosomal Activity Reported for 2-[4-[3-Chloro-4-(hydroxymethyl)-phenyl-1-piperazinyl]-1-phenylpropanones Administered in Single Oral Doses to Mice

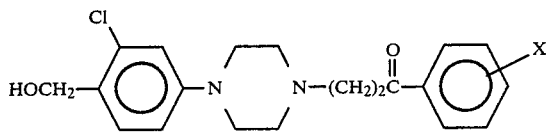

| Cpd. | X | mp (°C.) | Yield (%)[4] | % Reduction Live Worm Burden | | |
|---|---|---|---|---|---|---|
| | | | | 125 mg/kg | 40 mg/kg | 20 mg/kg |
| 28. | 4-Cl | 130–134 | 67 | 99[1] | 88,98[2] | 66 |
| 29. | H | 110–112.5 | 69 | 89 | 69 | |
| 30. | 4-CH$_3$ | 99–102 | 34 | 96 | 75 | |
| 31. | 4-SCH$_3$ | 131.5–134 | 77 | 93 | 73 | |
| 32. | 4-SO$_2$CH$_3$ | 126–128 | 75 | 91 | 84,72 | 43 |
| 33. | 4-CH(CH$_2$)$_5$ | 109–111 | 73 | 93 | 79 | |
| 34. | 4-OCH$_3$ | 120–122 | 23 | 93 | 39 | |
| 35. | 4-Cl,3-NO$_2$ | 162.5–164.5 | 75 | 98 | 79 | |
| 36. | 3,4-(CH=CH)$_2$ | 142–144 | 74 | 95 | 82,86 | 75 |
| 37. | 3-NH$_2$,4-Cl | 166.5–167.5 | 95[4] | 95 | 83,88 | 81 |
| 38. | 4-SOCH$_3$ | 103–107 | 36 | 91 | 73 | |
| 39. | 2,4-Cl$_2$ | 128–131 | 82 | 94 | 86,88 | 70 |
| 40. | 2,4-F$_2$ | 107–110 | 84 | 99 | 86,88 | 71 |
| 41. | 2,3,4-Cl$_3$ | 133–136 | 15 | 96 | 83,89 | 82 |
| 42. | 4-Br | 122–125 | 88 | 98 | 84,91 | 82 |
| 43. | 2,5-Cl$_2$ | 83–86 | 29 | 98 | 80,87 | 84 |
| 44. | 4-C$_6$H$_5$ | 145–149 | 11 | 97 | 89,89 | 69 |

[1]Dose, 156 mg/kg.
[2]Dose, 50 mg/kg.
[3]Yield of reaction of appropriate haloethylphenyl ketone with 1-[3-chloro-4-(hydroxymethyl)-phenyl] piperazine, unless otherwise noted.
[4]Yield on reduction of Cpd. 35.

TABLE 3

Antischistosomal Activity Reported For 4-[3-Chloro-4-(hydroxymethyl)-phenyl]-1-piperazinylheterocyclic-ethanones and -propanones Administered in Single Oral Doses to Mice

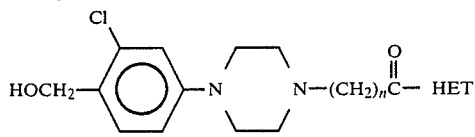

| Cpd. | n | HET | mp (°C.) | Yield (%)[3] | % Reduction Live Worm Burden | | |
|---|---|---|---|---|---|---|---|
| | | | | | 125 mg/kg | 40 mg/kg | 20 mg/kg |
| 45. | 1 | (thiophene) | 153–154 | 19 | 68 | 10 | |
| 46. | 1 | (furan) | 132–134 | 30 | 83[1] | 31[2] | |
| 47. | 1 | (5-Br-thiophene) | 153–154 | 59 | 93 | 35 | |
| 48. | 1 | (5-I-thiophene) | 167–168 | 28 | 30 | −20 | |
| 49. | 1 | (benzofuran) | 169–172 | 55 | 97 | 91,70 | 33 |

TABLE 3-continued

Antischistosomal Activity Reported For 4-[3-Chloro-4-(hydroxymethyl)-
phenyl]-1-piperazinylheterocyclic-ethanones and -propanones
Administered in Single Oral Doses to Mice

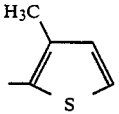

| Cpd. | n | HET | mp (°C.) | Yield (%)[3] | % Reduction Live Worm Burden | | |
| --- | --- | --- | --- | --- | --- | --- | --- |
| | | | | | 125 mg/kg | 40 mg/kg | 20 mg/kg |
| 50. | 1 | 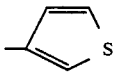 | 129–131 | 39 | 28 | −12 | |
| 51. | 1 | 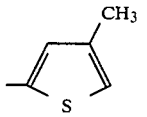 | 164–166 | 62 | 83 | −6 | |
| 52. | 1 | 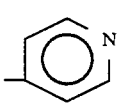 | 165–168 | 50 | 69 | 25 | |
| 53. | 1 | 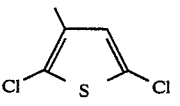 | 142–144 | 32 | 99 | 89,86 | 72 |
| 54. | 1 | 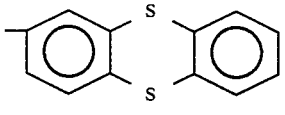 | 151–152 | 45 | 83 | 69 | |
| 55. | 1 | 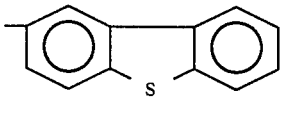 | 135–138 | 34 | 68 | 54 | |
| 56. | 1 | 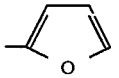 | 162–166 | 59 | 77 | 51 | |
| 57. | 2 |  | 95–98 | 67 | 98 | 85,87 | 60 |
| 58. | 3 |  | 132–133 | 48 | 77 | 20 | |

[1]Dose, 156 mg/kg.
[2]Dose, 50 mg/kg.
[3]Yield of reaction of appropriate a-haloalkylheterocyclic ketone with 1-[3-chloro-4-(hydroxymethyl)phenyl]piperazine.

TABLE 4

Antischistosomal Activity Reported For Phenyl Derivatives of
1-[3-Chloro-4(hydroxymethyl)phenyl]piperazine
Administered in Single Oral Doses to Mice

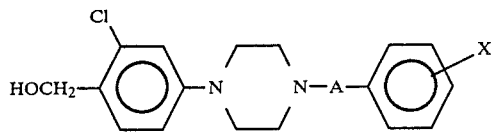

| Cpd. | A | X | mp (°C.) | Yield (%) | % Reduction Worm Burden 125 mg/kg | 40 mg/kg | 20 mg/kg |
|---|---|---|---|---|---|---|---|
| 59. | —(CH$_2$)$_3$C(=O)— | 4-Cl | 137–139 | 35[1] | 68 | 30 | |
| 60. | —(CH$_2$)$_3$C(=O)— | 3,4-(CH$_3$)$_2$ | 119.5–120.5 | 17[1] | 88 | 67 | |
| 61. | —CH$_2$C(OH)(CH$_3$)— | 4-Cl | 126–130 | 21[2] | 96 | 88,81 | 68 |

[1]Yield of reaction of appropriate halopropylphenyl ketone with 1-[3-chloro-4-(hydroxymethyl)phenyl]piperazine.
[2]Yield of reaction of cpd. 1 with methylmagnesium chloride.

Certain of the compounds were also tested in monkeys as follows:

A. Preinfection Procedure: The monkeys were kept under quarantine for a period of 45 days to test for tuberculosis, virus, and parasitic infections. When infections were found, specific therapy was given. At the end of 45 days the animals were entered into the main primate facility. The animals were then subjected to a two week conditioning period, during which time routine physical examinations were conducted.

B. Experimental Procedures: *Cebus apella* weighing between 1.5 and 3 kilograms were exposed percutaneously to 350 *S. mansoni* cercariae of the Walter Reed Army Institute of Research Laboratory Stock of Puerto Rican strain. Monkeys were caged individually. Throughout the experiment, they were observed for overt signs of intoxication such as: weakness, emesis, fecal consistency, ataxia, paralysis, anorexia, behavioral changes, general malaise, and weight loss. Weight determinations were made regularly. The daily food intake was monitored. Fecal examinations (Modified AMS III Technique) were conducted twice per week beginning at 28 days postexposure to *S. mansoni* cercariae.

At necropsy (120 days after treatment) schistosome worms were recovered by the Perf-O-Suction method. Following perfusion, the liver and intestine were removed and exmined for the presence of live and dead worms.

C. Drug Treatment: The compounds supplied by Warner-Lambert/Parke-Davis were suspended in aqueous 25% glycerol and 1% Cremophor. Treatment consisted of the drug administered orally in four equal doses over two days or as specified in Tables 6 and 6a.

D. Criteria Used to Evaluate Therapeutic Effectiveness:
1. The location, number and sex ratio of schistosomes.
2. The presence and viability of eggs appearing in the feces, intestine, and liver and necropsy as well as quantitative assay of eggs in feces.
3. Gross pathological appearance of test animal organs such as liver, spleen, intestine, kidney, lung, and pancreas.

TABLE 5

Antischistosomal Activity Against S. Mansoni Reported For Phenyl-
piperazine Derivatives in Cebus Apella Monkeys Treated Orally

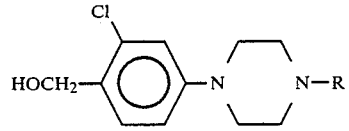

| R | Total Dose (mg/kg)[1] | Total Live Worms at Necropsy[2] | Normal Worms at Necropsy | % Reduction Live Worm Burden | Fecal Egg Count at Necropsy | Tissue Egg Viability |
|---|---|---|---|---|---|---|
| —(CH$_2$)$_2$CO—C$_6$H$_4$—Cl  Cpd. 28 | 400 | 6 | 0 | 97 | 0 | — |
| | 400 | 11 | 0 | 95 | 0 | — |
| | 200 | 0 | 0 | 100 | 0 | — |
| | 200 | 8 | 0 | 96 | 0 | — |
| | 100 | 15 | 0 | 93 | 0 | — |
| | 100 | 27 | 0 | 87 | 0 | — |

TABLE 5-continued

Antischistosomal Activity Against S. Mansoni Reported For Phenyl-piperazine Derivatives in Cebus Apella Monkeys Treated Orally

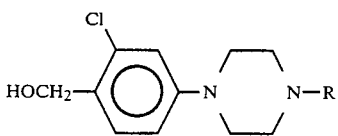

| R | Total Dose (mg/kg)[1] | Total Live Worms at Necropsy[2] | Normal Worms at Necropsy | % Reduction Live Worm Burden | Fecal Egg Count at Necropsy | Tissue Egg Viability |
|---|---|---|---|---|---|---|
| —CH₂CO— (2,3,4-trichlorophenyl) Cpd. 8 | 400 | 1 | 0 | 99 | 0 | — |
|  | 400 | 4 | 0 | 98 | 0 | — |
|  | 200 | 31 | 0 | 85 | 0 | — |
|  | 200 | 35 | 0 | 83 | 0 | — |
| —CH₂CO— (benzofuran) Cpd. 49 | 360 | 42 | 0 | 80 | 0 | — |
|  | 360 | 28 | 2 | 87 | 0 | + |
| Sham Dosed | — | 217 | 217 | 0 | 25 | + |
| Controls | — | 188 | 188 | 0 | 14 | + |

[1]Experimental drugs given in four equal doses over two days. Oltipraz given in two equal dose 12 hours apart.
[2]Most of the worms recovered from the treated monkeys were stunted femals found in the mesenteric veins.

Tests were also conducted for bacterial mutagenicity and the results are reported in Table 6. The tests were carried out as follows:

Four phenylpiperazine derivatives were selected and specially purified samples were prepared for testing as bacterial mutagens. The tests were conducted with five strains (TA98, TA100, TA1535, TA1537, and TA1538) of *Salmonella Typhimurium*. The compounds were the base of cpd. A (Table 6a), cpd. 28 (Table 2), cpd. 49 (Table 3), and cpd. 8 (Table 1). Hycanthone was used as a positive control drug. In the initial test, cpd. A base was nonmutagenic, confirming previous work using strains TA98 and TA100 with cpd. A. Cpd. 28 and cpd. 8 were mutagenic, but much less so than hycanthone. In this initial test, cpd. 49 was weakly mutagenic for strain TA98 with microsomal activation, but nonmutagenic for the other four strains. A second test (not shown in Table 6) using TA98 and microsomal activation with additional concentrations in the high range (10–60 micrograms/ml) did not confirm this mutagenicity. Therefore, it was concluded that cpd. 49 is nonmutagenic in the Ames/Salmonella assay.

TABLE 6

Summary of the Mutagenicities of A-free base, Cpds. 28, 8, 49 and Hycanthone

| Sample | Metabolic Activation | Salmonella Strains* | | | | |
|---|---|---|---|---|---|---|
|  |  | TA98 | TA100 | TA1535 | TA1537 | TA1538 |
| Cpd. 28 | + | — | + | NT | — | + |
|  | — | — | — | NT | — | w+ | w+ |
| Cpd. 8 | + | — | + | NT | w+ | — |
|  | — | — | — | NT | — | — |
| Cpd. 49 | + | + | — | NT | — | — |
|  | — | — | — | NT | — | — |
| Hycan-thone | + | + | + | NT | + | + |
|  | — | — | + | + | — | + | + |

TABLE 6-continued

Summary of the Mutagenicities of A-free base, Cpds. 28, 8, 49 and Hycanthone

| Sample | Metabolic Activation | Salmonella Strains* | | | | |
|---|---|---|---|---|---|---|
|  |  | TA98 | TA100 | TA1535 | TA1537 | TA1538 |

+: Positive Response
—: Negative Response
w+: Weak Positive Response
NT: Not Tested.

Thus, while U.S. Pat. No. 4,234,583 indicates that the N-oxide moiety is required for the absence of bacterial mutagenic activity in phenylpiperazines with small alkyl groups for side chains, it has now been demonstrated that N-oxidation is not a requirement for nonmutagenicity throughout the entire phenylpiperazine class, especially for selected analogs covered herein.

It will be understood that the specification and examples are illustrative but not limitative of the present invention and that other embodiments within the spirit and scope of the invention will suggest themselves to those skilled in the art.

We claim:

1. 2(4-(3-Chloro-4-hydroxymethylphenyl)-1-piperazinyl)-1-(2,3,4-trichloro-phenyl)-ethanone of the formula

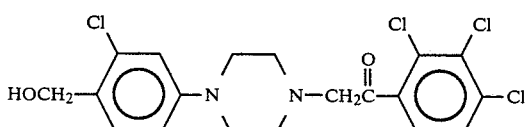

or a pharmacologically acceptable salt thereof.

2. 2-(4-(3-Chloro-4-hydroxymethylphenyl)-1-piperazinyl)-1-(2-benzofuranyl)-ethanone of the formula

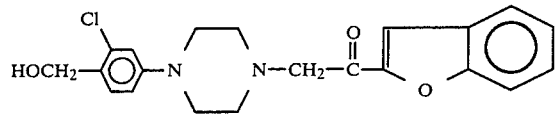

or a pharmacologically acceptable salt thereof.

3. A method of combating a schistosomal infection in a patient which comprises administering to such patient an antischistosomal effective amount of a compound of the formula

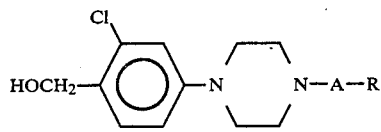

in which

A is

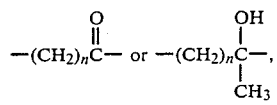

n is 1, 2 or 3, and

R is phenyl optionally substituted with halogen, alkyl, phenyl, cyano, hydroxy, alkoxy, mercapto, sulfinyl, sulfonyl, amino, nitro, trifluoromethyl and/or naphthyl radicals; or a furan, thiophene, pyridine, benzofuran, dibenzothiophene or thianthrene radical optionally substituted by halogen and/or alkyl of up to 4 carbon atoms, or a pharmaceutically acceptable salt thereof.

4. The method according to claim 3 wherein such compound is
2(4-(3-chloro-4-hydroxymethylphenyl)-1-piperazinyl)-1-(2,3,4-trichlorophenyl)-ethanone,
2-(4-(3-chloro-4-hydroxymethylphenyl)-1-piperazinyl)-1-(4-chlorphenyl)-propanone or
2-(4-(3-chloro-4-hydroxymethylphenyl)-1-piperazinyl-1-(2-benzofuryl)-ethanone, or a pharmacologically acceptable salt thereof.

* * * * *